United States Patent [19]

Anderson

[11] Patent Number: 5,372,581
[45] Date of Patent: Dec. 13, 1994

[54] METHOD AND APPARATUS FOR PLACENTAL BLOOD COLLECTION

[75] Inventor: Sanford J. Anderson, Eden Prairie, Minn.

[73] Assignee: Minneapolis Children's Services Corporation, Minneapolis, Minn.

[21] Appl. No.: 95,269

[22] Filed: Jul. 21, 1993

[51] Int. Cl.⁵ .................... A61M 1/00; A61M 5/00; A61D 1/10
[52] U.S. Cl. .................... 604/32; 604/248; 606/120
[58] Field of Search .................... 604/30, 32, 33, 246, 604/248, 249; 606/120; 128/762, 703

[56] References Cited

U.S. PATENT DOCUMENTS

| | | | |
|---|---|---|---|
| 2,485,842 | 10/1949 | Pennington | 604/248 X |
| 2,842,124 | 7/1958 | James | 604/248 X |
| 2,973,761 | 3/1961 | Kohl | 606/120 X |
| 3,048,192 | 8/1962 | Murphy, Jr. | 604/248 X |
| 3,157,201 | 11/1964 | Littmann | 604/32 X |
| 3,344,785 | 10/1967 | Hamilton | 128/214 |
| 3,678,960 | 7/1972 | Leibinsohn | 604/248 X |
| 3,834,372 | 9/1974 | Turney | 604/248 X |
| 3,965,896 | 6/1976 | Swank | 128/214 |
| 4,397,335 | 8/1983 | Doblar et al. | 137/625.19 |
| 4,428,374 | 1/1984 | Auburn | 606/120 X |
| 4,447,235 | 5/1984 | Clarke | 604/169 |
| 4,744,785 | 5/1988 | Rosenthal et al. | 604/4 |
| 4,781,188 | 11/1988 | Collins | 606/120 |
| 4,900,322 | 2/1990 | Adams | 604/410 |
| 5,053,025 | 10/1991 | Knippscheer | 604/317 |
| 5,059,168 | 10/1991 | Stone | 604/4 |
| 5,097,842 | 3/1992 | Bonn | 128/762 |
| 5,104,387 | 4/1992 | Pokorney et al. | 604/248 |
| 5,114,672 | 5/1992 | Knippscheer et al. | 122/41 |
| 5,190,556 | 3/1993 | Hessel | 606/120 |

OTHER PUBLICATIONS

*Retrieval of Placental Blood from the Imbilical Vein to Determine Volume, Sterility, and Presence of Clot Formation*, American Journal of Diseases of Children, Jan. 1992, vol. 146, pp. 36–39.

*Transfusion Medicine Fraces Time of Major 'Challenges and Changes'*, JAMA, Aug. 12, 1992, vol. 268, No. 6, pp. 697–700.

Primary Examiner—John D. Yasko
Assistant Examiner—Adam J. Cermak
Attorney, Agent, or Firm—Merchant, Gould, Smith, Edell, Welter & Schmidt

[57] ABSTRACT

The present invention relates to an apparatus and a method for the withdrawal of placental blood from an umbilical cord vein. More specifically, the apparatus has a valve housing and a valve member. A needle is attached to a first port in the valve housing and a blood collection bag is attached to a second port in the valve housing. Additionally, a first syringe is attached to a third port, and a second syringe is attached to a fourth port. When the plunger on the first syringe is withdrawn it causes blood to flow from the umbilical vein through the needle and into the syringe. The valve member is then rotated, thereby sealing the needle from the blood collection bag and the syringes. Subsequently, the plunger in the second syringe, which contains an anticoagulant, is pressed. This causes the anticoagulant to mix with the blood. The blood is then stored in the attached storage bag.

20 Claims, 5 Drawing Sheets

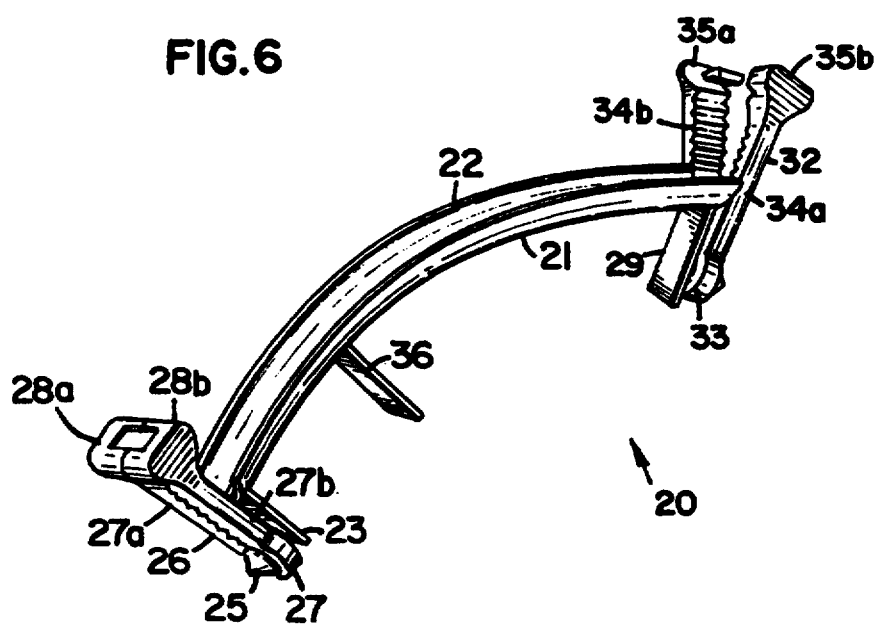

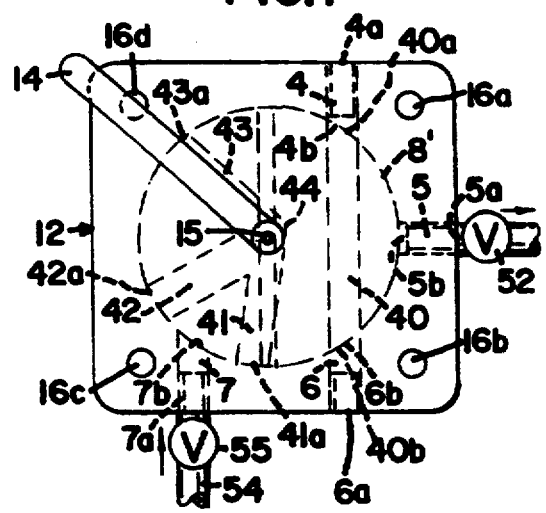
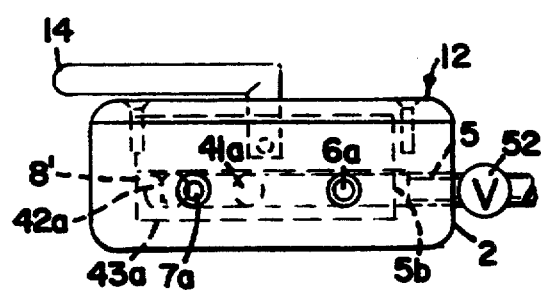

METHOD AND APPARATUS FOR PLACENTAL BLOOD COLLECTION

TECHNICAL FIELD

The present invention relates generally to a method and apparatus for the purpose of withdrawal of the placental blood from an umbilical vessel (artery or vein) prior to the delivery of the placenta and under sterile conditions and more particularly to a method and apparatus which will also permit the anticoagulation of the placental blood, identification of the placental blood volume, and its storage.

BACKGROUND

Autologous transfusion, that is blood taken from an individual and given back to that same individual at a later time, is a common practice in several surgical specialties. Examples include cardiovascular and orthopedic surgery. In an emergency setting, this process has also been used in the neonatal or newborn population. The interest in finding options to the use of homologous bank blood for the transfusion of premature infants has increased in recent years. An estimated 38,000 premature neonates at or below 1500 grams birth weight are born annually in the United States. Eighty percent of these neonates will require multiple red cell transfusions.

One researcher has calculated that multitransfused infants are typically exposed to eight different donors. Sacher, Transfus Med Rev 1989;3;39–54. Another researcher has conducted two different studies each of which has determined that 9.5% and 6.2%, respectively, of infants who receive a transfusion actually receive infected blood. Strauss, Transfusion 1989;26:419–22. Concern over the exposure of this population of sick neonates to infectious agents such as HIV; CMV; and Hep A, B and C, have led to the interest in developing options to the use of homologous bank blood in sick premature infants. These options include using a single donor from a blood bank or a directed family member, using an extended storage media and/or a multi-bag storage system, using recombinant erythropoietin to stimulate the neonates own marrow to manufacture red cells, and using autologous placental blood harvested at the time of delivery.

The use of placental blood is promising because the placenta can provide an adequate volume of blood for at least one 10 ml/kg transfusion in 87% of the cases. Sanford Anderson et al., *Retrieval of Placental Blood From the Umbilical Vein to Determine Volume, Sterility, and Presence of Clot Formation*, 146 AJDC 36–39 (January 1992). In addition to the possible use of placental blood for autologous transfusions, researchers are also exploring potential uses of specific elements of placental blood, e.g., removal of the white blood cells for storage and possible administration to the patient or a relative in the future as an alternative to a bone marrow transplant.

The use of placental blood has had the following limitations: safety of removal; sterility of the blood upon removal and storage; anticoagulation of the blood with the appropriate agent in time to prevent clotting of the specimens; minimizing trauma to the placenta and cord to limit the tissue damage and release of cell contents which might contaminate the placental blood; and efficiency of removal of the blood from the umbilical vessel. In fact, placental blood that is used for transfusion has a bacterial contamination rate of 12%. Sanford Anderson et al., *Retrieval of Placental Blood From the Umbilical Vein to Determine Volume, Sterility, and Presence of Clot Formation*, 146 AJDC 36–39 (January 1992). This bacterial contamination is usually a result of organisms that are on the surface of the umbilical vein.

As described below, elements of the present invention are unique and different from the existing prior art devices in light of the recognition of limitations as enumerated above.

The elimination of bacterial contamination of the placental blood, the need to minimize tissue damage by external forces such as pressure, and the need to properly anticoagulate the placental blood are critical if placental blood is to be used at a later date. The longer a placenta is exposed to the birth canal after the delivery of the infant, and the more manipulation it undergoes during the delivery process or later in a mechanical device, the greater the risk for the above complications to occur. The present invention is an improvement over the Knippscheer et al. device (U.S. Pat. No. 5,053,025) because it is designated to allow withdrawal of the placental blood from the umbilical vessel immediately after the delivery of the infant and before the delivery or manipulation of the placenta while it still resides within the uterus. In addition, the present invention uses the umbilical cord holder to position the umbilical vessel allowing the proper cleansing of its surface and the sterile withdrawal of the placental blood. Unlike the present invention, Knippscheer et al. allows the placental blood to "drain" from the contamination end of the cut placental cord.

The present invention also includes a valve system which allows the operator to serially remove placental blood and mix it with the appropriate volume and type of anticoagulant and transfer that mixture to an appropriate storage bag all within a closed sterile system and with minimal mechanical motion by the operator. This is an improvement over the Bonn device (U.S. Pat. No. 5,097,842) which does not allow for the variability in volume of blood obtained from infant to infant. Applicant has discovered in his research that it is critical to be able to mix the proper amount of anticoagulant with the volume of placental blood that is present. The manipulation of the withdrawal system must be minimal or the operator will inadvertently withdraw the needle from the umbilical vessel allowing loss or contamination of the placental blood. The combination of an umbilical cord holder and the valve system in the present invention addresses these issues.

The present invention is an improvement over Stone's device U.S. Pat. No. 5,059,168) because of its use of the umbilical cord holder, and the fact that the syringe must be in line with the axis of the umbilical vessel to allow one operator to carry out the operation of the placental blood withdrawal.

Hamilton (U.S. Pat. No. 3,344,785) and Clarke (U.S. Pat. No. 4,447,235) both disclose the use of a simple three way stopcock system which is not sufficient to allow the withdrawal of the placental blood, the admixture of the appropriate anticoagulant, and the transfer of that mixture to a storage bag all within a closed sterile system.

SUMMARY

The present invention is an apparatus and method for the withdrawal of placental blood. It is advantageous because it minimizes the risk of contaminating the placental blood. More particularly, the present invention has a valve housing having an outer periphery and an inner cavity. The valve housing has a first, second, third, and fourth channel all having outer ports and inner ports, the outer ports proximate the outer periphery and the inner ports proximate the inner cavity. A valve member is positioned for movement within the inner cavity and there are means for moving the valve member to a plurality of positions.

A further embodiment of the present invention has an umbilical cord holder having a curved trough. The curved trough has a first end, a second end, an open top, and a bottom surface. The curved trough is needle resistant and sized to hold an umbilical cord. The umbilical cord holder further has a stem having first and second ends, the first end operably connected to the bottom surface of the curved trough. A clamp is operably connected to one end of the curved trough. The clamp is capable on constricting a region of the umbilical cord so that fluid cannot pass through the constricted region. The umbilical cord holder may further include a second clamp operably connected to the second end of the curved trough. The second clamp is also capable of constricting a region of the umbilical cord so that fluid cannot pass through the constricted region.

The method of withdrawing blood from a placenta includes the following steps. A needle resistant trough is placed in a first hand. An umbilical cord is then placed on the trough and the cut end of the umbilical cord is clamped. Cleansing of the cord is then carried out with an appropriate anti-bacterial agent. Next, the needle of the blood collection device is inserted into the umbilical cord while holding a blood collection device in a second hand. The blood collection device is operated with the second hand in order to withdraw blood into a collection syringe. Anticoagulant is then added to the collection syringe by use of the second hand, and the blood from the collection syringe is transferred to a storage bag by operation of the second hand.

DESCRIPTION OF THE DRAWINGS

FIG. 6 is a perspective view of the umbilical cord holder.

FIG. 7 is a top elevational view of an alternative embodiment of the valve with hidden lines showing the disk and channels.

FIG. 8 is a side elevational view of the alternative embodiment of the valve with hidden lines showing the disk and channels.

DETAILED DESCRIPTION

Figure 1:
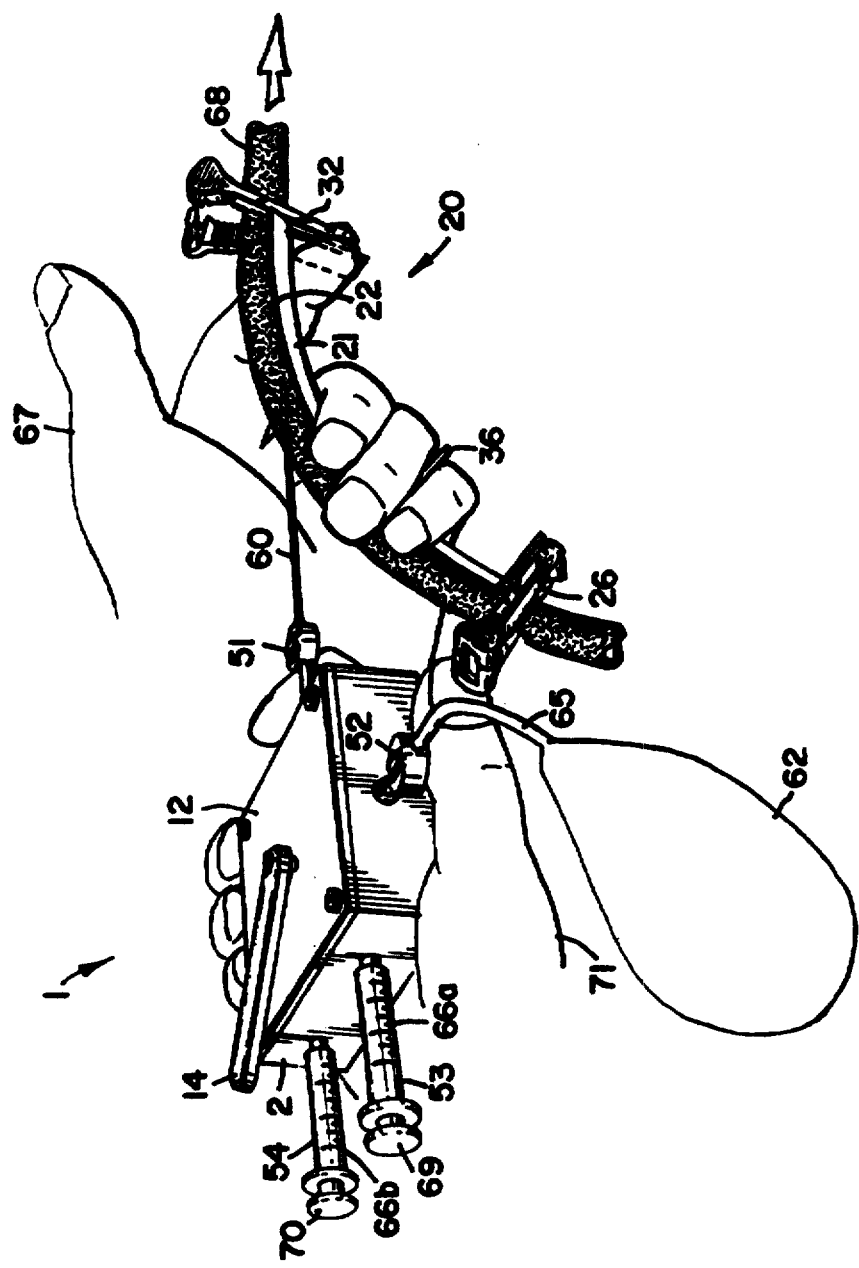
FIG. 1 is a perspective view of the system and method for withdrawing placental blood.

A preferred embodiment of the invention will be described in detail with reference to the drawing, wherein like reference numerals represent like parts and assemblies throughout the several views.

Referring now to the figures, there is illustrated preferred embodiments of the apparatus for placental blood collection that includes the principles of the present invention. The apparatus includes a valve 1 that is generally shown in FIGS. 1–5. The valve includes a housing 2 that has a central cavity 3 that is cylindrical in shape and has a single open end 50. The housing has a first channel 4 that has an outer port 4a and an inner port 4b, a second channel 5 that has an outer port 5a and an inner port 5b, a third channel 6 that has an outer port 6a and an inner port 6b, and a fourth channel 7 that has an outer port 7a and an inner port 7b. Outer ports 4a, 5a, 6a, and 7a all have threads, not shown, capable of receiving mating threads or flanges that are located on syringes, one-way valves, needles, or an orifice on a blood storage bag. Alternately, the components may be glued or otherwise secured to the outer ports.

Figure 2:
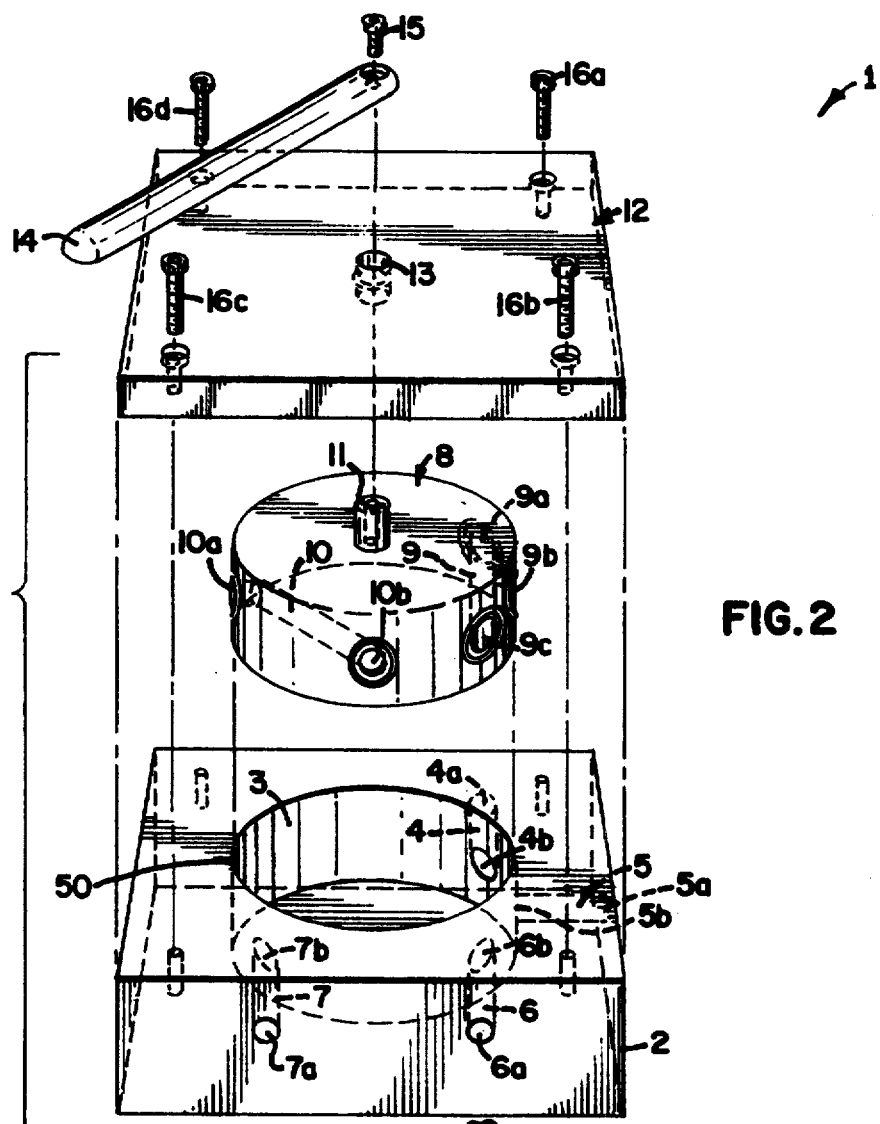
FIG. 2 is an exploded view of the valve with hidden lines showing the channels.
Figure 3:
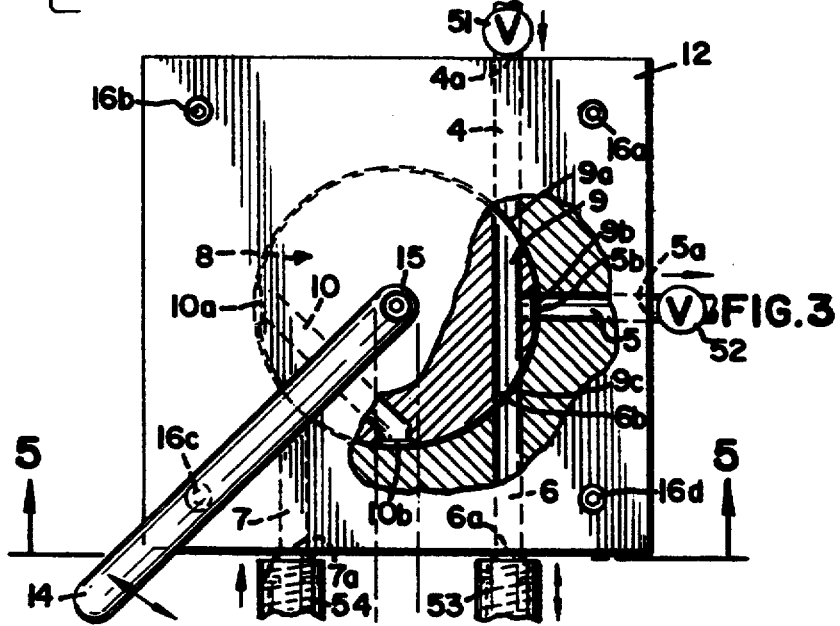
FIG. 3 is a top elevational view of the valve with the dish in its first position and a break out showing the dish and some channels and hidden lines showing the disk and some channels.

Disk 8 is located within cavity 3 and has a diameter that is slightly smaller than the diameter of the cavity 3 so that disk 8 may rotate. Disk 8 has a fifth channel 9 that has a T configuration and three ports 9a, 9b, and 9c. As shown in FIGS. 2 and 3, the fifth channel 9 is oriented in the disk 8 so that when the disk 8 is in a first position, port 9a mates with inner port 4b, port 9b mates with inner port 5b, and port 9c mates with inner port 6b. Disk 8 also includes sixth channel 10 that has two ports 10a and 10b.

Figure 4:
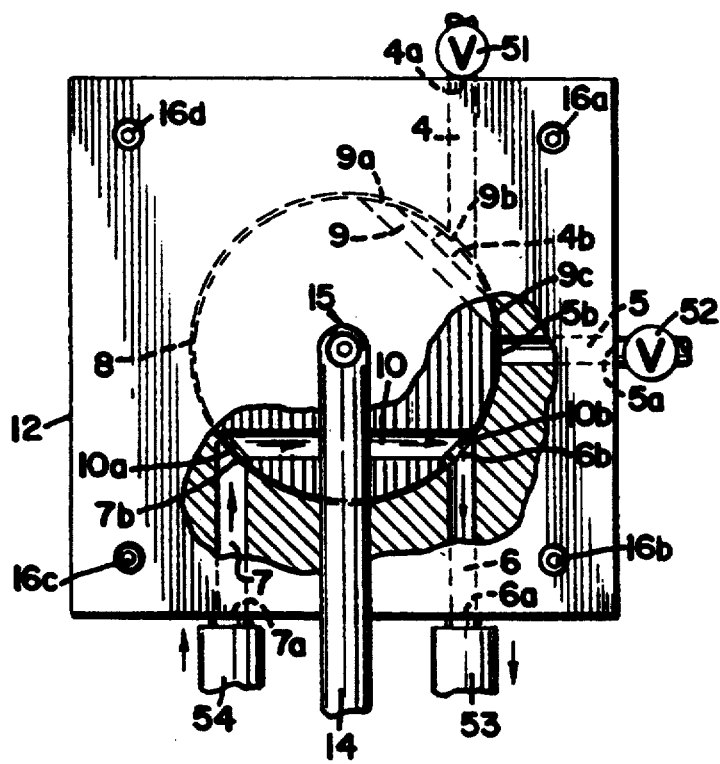
FIG. 4 is a top elevational view of the valve with the dish in its second position and a break out showing the disk and some channels and hidden lines showing the disk and some channels.
Figure 5:
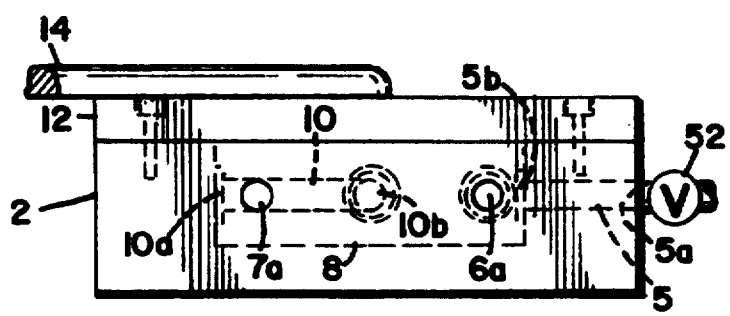
FIG. 5 is a side elevational view of the valve along lines 5—5 as shown in FIG. 3 with hidden lines showing the disk and channels.

When the disk is in a second position, as shown in FIG. 4, sixth channel 10 is oriented so that ports 10a and 10b mate with inner ports 7b and 6b, respectively, and ports 9a, 9b, and 9c are disengaged from inner ports 4b, 5b, and 6b. When the disk 8 is in the first position, the sixth channel 10 is not in fluid communication with the fourth channel 7 or the third channel 6. When the disk 8 is in the second position, the sixth channel 10 is in fluid communication with the fourth channel 7 and the third channel 6. In this second position, the fifth channel 9 is not in fluid communication with the first channel 4, the second channel 5, or the third channel 6. Finally, disk 8 has a shaft 11 that extends from the top of the disk 8 along its axis. The valve 1 has a plate 12 that covers the cavity 3 and secures the disk 8 within the cavity 3. The plate 12 has a hole 13 through which shaft 11 extends from disk 8. Handle 14 is attached to shaft 11 by screw 15 so that disk 8 rotates as handle 14 is moved from one position to another. Plate 12 is attached to housing 2 by screws 16a, 16b, 16c, and 16d.

As shown in FIG. 1, one-way valve 51 is connected between outer port 4a and needle 60. One-way valve 51 is oriented so that fluid may flow from needle 60 into channel 4, but fluid may not flow from channel 4 back through needle 60. Needle 60 is attached to one-way valve 51 by means of threads. In turn, one-way valve 51 is attached to port 4a by means of threads. A second one-way valve 52 is connected between outer port 5a and storage bag 62 which is for storing a blood and anticoagulant mixture. One-way valve 52 is oriented so that fluid may flow into the storage bag 62, but fluid may not flow from the storage bag 62 back into channel 5. Storage bag 62 has a tube 65 that fits around a port on one-way valve 52. In turn, one-way valve 52 is attached to outer port 5a by means of threads. Preferably, one-way valves 51 and 52 are model number BC-1000 manufactured by Burron Medical, Inc. of 824 12th Avenue, Bethlehem, Pa. 18018 and needle 60 is model number 5199 manufactured by Becton Dickenson and Company of Rutherford, N.J. 07070.

Finally, blood collection syringe 53 is attached to outer port 6a and anticoagulant syringe 54 is attached to outer port 7a. Blood collection syringe 53 and anticoagulant syringe 54 both include indicia of measurement 66a and 66b, respectively. Additionally, blood collection syringe 53 and anticoagulant syringe 54 include threads, not shown, that are capable of mating with the threads of outer ports 6a and 7a.

In FIG. 6, an umbilical cord holder is shown generally as 20. The umbilical cord holder 20 has a curved trough 21 that has an open top 22. Curved trough 21 is made of a needle resistent material such as stainless steel, which can be sterilized. A flange 23 extends downward from the first end of the trough 21 and is attached by suitable means such as a weld. A shaft, not shown, extends outward from flange 23 and has a cap 25. The shaft, not shown, and cap 25 are preferably a rivet that is easily secured to flange 23. Cut-end umbilical cord clamp 26 has a curved end 27 that snap locks around the shaft. Cut-end umbilical cord clamp 26 also has clamping portions 27a and 27b. The inside surfaces of clamping portions 27a and 27b is lined with small ribs. Finally, clamp 26 has a fastener with a male end 28a and a female end 28b mounted at the end of clamping portion 27a and 27b, respectively. The opposite end of the trough 21 has an identical clamping mechanism that is comprised of flange 29, uncut-end umbilical cord clamp 32, circular end 33, clamping portions 34a and 34b, male fastener 35a, and female fastener 35b. This opposite end also has a rivet, not shown, that forms a shaft and a cap. Preferably, clamps 26 and 32 are model number 31-041 Cord Clamp manufactured by Qualtex, a division of De Royal Industries, Inc., of Powell, Tenn. 37849. Stem 36 extends downward from trough 21 and is located at a distance from cut-end umbilical clamp 26 and flange 23 sufficient to allow a person to insert their little finger between flange 23 and stem 36.

As shown in FIG. 1, in order to collect placental blood, the umbilical cord holder 20 is placed in one hand 67 such that the stem 36 is located between the little and fourth fingers. The stem allows the umbilical cord holder 20 to be easily grasped and maneuvered. The other hand 71 is then available to clamp the umbilical cord 68 and manipulate the valve 1. The umbilical cord 68 is then placed in trough 21 so that the umbilical cord 68 extends from the placenta through uncut-end umbilical cord clamp 32, the trough 21, and the cut-end clamp 26. Clamping portions 27a and 27b of cut-end clamp 26 are then squeezed together so that male and female fasteners 28a and 28b secure together thereby restricting the umbilical cord. The umbilical cord is then cleansed by a suitable anti-bacterial agent. Needle 60 is then inserted into a vein of the umbilical cord that is lying in trough 21. After needle 60 is inserted into the umbilical cord, the disk 8 must be oriented in its first position so that port 9a is aligned with inner port 4b, port 9b is aligned with inner port 5b, and port 9c is aligned with inner port 6b. The plunger 69 of the blood collection syringe 53 is then withdrawn thereby causing blood to flow from the placenta through a vein in the umbilical cord, the needle 60, the one-way valve 51, the first channel 4, the fifth channel 9, the third channel 6, and into the blood collection syringe 53. Handle 14 is then turned so that disk 8 rotates into its second position and causes the fifth channel 9 to disengage and the sixth channel 10 to engage so that port 10a is aligned with inner port 7a and port 10b is aligned with inner port 6b. The plunger 70 on the anticoagulant syringe 54 is then depressed thereby causing the anticoagulant to flow from the anticoagulant syringe through the fourth channel 7, through the sixth channel 10, through the third channel 6, and into the blood collecting syringe 53 thereby causing the blood and the anticoagulant to mix.

Handle 14 is then rotated in order to return disk 8 to its first position. As a result, ports 9c, 9b, and 9a mate with inner ports 6b, 5b, and 4b, respectively. The plunger 69 of the blood collection syringe 53 is then depressed, which causes the blood and anticoagulant mixture to flow through the third channel 6, through the fifth channel 9, through the second channel 5, through one-way valve 52, and into the storage bag 62. One-way valve 51 prevents the blood and anticoagulant mixture from flowing back through needle 60 into the umbilical cord 68. After the necessary amount of blood is withdrawn from the placenta, the uncut-end umbilical cord clamp 32 is closed.

An alternative embodiment of disk 8 is represented in FIGS. 7 and 8. In this alternative embodiment, disk 8' has a fifth channel 40 with a first port 40a and a second port 40b, a sixth channel 41 with a port 41a, a seventh channel 42 with a port 42a, and an eighth channel 43 with a port 43a. The sixth channel 41, seventh channel 42, and eighth channel 43 meet at junction 44 in the center of disk 8'. Thus, sixth channel 41, seventh channel 42, and eighth channel 43 are all in fluid communication with one another. As shown in FIG. 7, when the disk is in a first position, the fifth channel 40 is aligned with the first channel 4 and the third channel 6; thus port 40a mates with inner port 4b, and port 40b mates with inner port 6b.

When the disk 8 is rotated into a second position, the sixth channel 41 is aligned with the second channel 5, the seventh channel 42 is aligned with the third channel 6, and the eighth channel 43 is aligned with the fourth channel 7. In the second position, therefore, port 41a mates with inner port 5b, port 42a mates with inner port 6b, and port 33a mates with inner port 7b.

Furthermore, in the alternative embodiment, one-way valve 51 is not required to be connected between port 4a and needle 60. In this instance, needle 60 is connected directly to outer port 4a by means of mating threads. However, one-way valve 55 is required to be connected between outer port 7a and anticoagulant syringe 54. One-way valve 55 is oriented so that it permits anticoagulant from the anticoagulant syringe 54 to flow into channel 7, but does not allow any fluid to flow from channel 7 into the anticoagulant syringe 54. In this instance, one-way valve 55 is attached to outer port 7a by means of mating threads. In turn, anticoagulant syringe 54 is attached to one-way valve 55 by means of mating threads.

When using the second embodiment, the umbilical cord 68 is initially placed in the holder 20 and the cut-end of the umbilical cord is clamped with cut-end clamp 26 as previously described. Disk 8 is then oriented in its first position so that port 40a mates with inner port 4b and point 40b mates with inner port 6b. The blood is then withdrawn from the umbilical cord. After this is accomplished, handle 14 is moved so that the disk 8 rotates into the second position thereby mating port 41a with inner port 7b, port 42a with inner port 6b, and port 43a with inner port 5b. The plunger 70 for the anticoagulant syringe is then depressed causing the anticoagulant to flow into the blood storage bag and the blood collecting syringe 53. The plunger 69 of the blood collecting syringe 53 is then depressed thereby causing the blood to flow into the blood storage bag 62. One-way valve 55 prevents the blood and anticoagulant mixture from flowing back into anticoagulant syringe 54.

While the invention has been described in conjunction with a specific embodiment thereof, it is evident that different alternatives, modifications, and variations will be apparent to those skilled in the art in view of the foregoing description. Accordingly, the invention is not limited to these embodiments or the use of elements having specific configurations and shapes as presented herein.

I claim:

1. An apparatus for withdrawal of blood from a body, the apparatus comprising:
   a) a valve housing having an outer periphery and an inner cavity;
   b) the valve housing having a first channel having an outer port and an inner port, the outer port proximate the outer periphery and the inner port proximate the inner cavity;
   c) the valve housing having a second channel having an outer port and an inner port, the outer port proximate the outer periphery and the inner port proximate the inner cavity;
   d) the valve housing having a third channel having an outer port and an inner port, the outer port proximate the outer periphery and the inner port proximate the inner cavity;
   e) the valve housing having a fourth channel having an outer port and an inner port, the outer port proximate the outer periphery and the inner port proximate the inner cavity;
   f) a valve member positioned for movement within the inner cavity;
   g) means for moving the valve member to a plurality of positions;
   h) means for selectively placing the first, second, third, and fourth channels in fluid communication, wherein fluid is flowable through the first channel to the third channel, from the second channel to the third channel, or from the third channel to the fourth channel; and
   i) a needle for withdrawing blood from the body, the needle in fluid communication with the outer port of the first channel;
   j) a bag for storing blood, wherein the bag is in fluid communication with the outer port of the second channel, further wherein the bag is detachable; and
   k) means for causing the placental blood to flow from the needle and into the bag.

2. The apparatus of claim 1 wherein the valve member has a first and a second position, the means for selectively placing comprising a fifth channel and a sixth channel, the fifth channel providing fluid communication between the first channel, the second channel, and the third channel when the valve member is in the first position and the sixth channel providing fluid communication between the third channel and the fourth channel when the valve member is in the second position.

3. The apparatus of claim 2 further comprising a one-way valve in fluid communication with the outer port of the first channel, the one-way valve permitting fluid to pass through the outer port and into the first channel.

4. The apparatus of claim 3, the apparatus further comprising means for mixing the blood with an anticoagulant.

5. The apparatus of claim 4 wherein the means for causing the blood to flow is a first syringe that is in fluid communication with the outer port of the third channel, the syringe capable of creating a vacuum.

6. The apparatus of claim 5 wherein the means for mixing the blood with an anticoagulant is a second syringe that is in fluid communication with the outer port of the fourth channel.

7. The apparatus of claim 1 wherein the valve member has a first and a second position, the means for selectively placing comprising a fifth channel and a sixth channel, the fifth channel providing fluid communication between the first channel and the third channel when the valve member is in the first position and the sixth channel providing fluid communication between the second channel, the third channel, and the fourth channel when the valve member is in the second position.

8. The apparatus of claim 7 wherein the valve member is a disk that is rotatable to a plurality of positions within the cavity.

9. The apparatus of claim 8 further comprising a handle generally connected to the disk so that the disk rotates when the handle is moved.

10. The apparatus of claim 9 further comprising a one-way valve in fluid communication with the outer port of the fourth channel, the one-way valve permitting fluid to pass through the outer port and into the fourth channel.

11. The apparatus of claim 10 the apparatus further comprising:
    a) a needle for withdrawing blood from the body, the needle in fluid communication with the outer port of the first channel;
    b) means for storing blood that is withdrawn from the body;
    c) means for causing the placental blood to flow from the needle and into the means for storing blood; and
    d) means for mixing the blood with an anticoagulant.

12. The apparatus of claim 11 wherein the means for causing the blood to flow is a first syringe that is in fluid communication with the outer port of the third channel, the syringe capable of creating a vacuum.

13. The apparatus of claim 12 wherein the means for mixing the blood with an anticoagulant is a second syringe that is in fluid communication with the outer port of the fourth channel.

14. The apparatus of claim 13 wherein the means for storing blood is a bag that is in fluid communication with the outer port of the second channel, the bag being detachable.

15. An apparatus for the withdrawal of placental blood from an umbilical cord, the apparatus comprising:
    a) a valve housing having an outer periphery and an inner cavity;
    b) the valve housing having a first channel having an outer port and an inner port, the outer port proximate the outer periphery and an inner port proximate the inner cavity;
    c) the valve housing having a second channel having an outer port and an inner port, the outer port proximate the outer periphery and an inner port proximate the inner cavity;

d) the valve housing having a third channel having an outer port and an inner port, the outer port proximate the outer periphery and an inner port proximate the inner cavity;

e) the valve housing having a fourth channel having an outer port and an inner port, the outer port proximate the outer periphery and an inner port proximate the inner cavity;

f) a disk positioned for movement within the inner cavity;

g) means for moving the disk to a plurality of positions;

h) means within the disk for selectively placing the first, second, third, and fourth channels is fluid communication, wherein fluid is flowable through the first channel, from the second channel to the third channel, or fluid is flowable from the third channel to the fourth channel;

i) an umbilical cord holder having a curved trough, the curved trough having a first end, a second end, an open top, and a bottom surface, the curved trough being needle resistant and sized to hold an umbilical cord;

j) a stem having first and second ends, the first end operatively connected to the bottom surface of the curved trough, wherein the stem allows a user to hold and maneuver the umbilical cord holder during use;

k) a first claim operably connected to the first end of the curved trough, the first clamp capable of constricting a region of the umbilical cord so that fluid cannot pass through the constricted region; and l) a second clamp operably connected to the second end of the curved trough, the second clamp capable of constricting a region of the umbilical cord so that the fluid cannot pass through the constricted region.

16. An apparatus for withdrawal of blood from a body, the apparatus comprising:

a) a valve housing having an outer periphery and an inner cavity;

b) the valve housing having a first channel having an outer port and an inner port, the outer port proximate the outer periphery and the inner port proximate the inner cavity;

c) the valve housing having a second channel having an outer port and an inner port, the outer port proximate the outer periphery and the inner port proximate the inner cavity;

d) the valve housing having a third channel having an outer port and an inner port, the outer port proximate the outer periphery and the inner port proximate the inner cavity;

e) the valve housing having a fourth channel having an outer port and an inner port, the outer port proximate the outer periphery and the inner port proximate the inner cavity;

f) a valve member positioned for movement within the inner cavity;

g) means for moving the valve member to a plurality of positions;

h) means for selectively placing the first, second, third, and fourth channels in fluid communication, wherein fluid is flowable through the first channel to the third channel, from the second channel to the third channel, or from the third channel to the fourth channel; and i) a needle for withdrawing blood from the body, the needle in fluid communication with the outer port of the first channel;

j) a first syringe that is in fluid communication with the outer port of the third channel, the first syringe for causing the placental blood to flow from the needle and into the means for storing blood; and k) a second syringe that is in fluid communication with the outer port of the fourth channel, the second syringe for mixing the placental blood with an anticoagulant.

17. The apparatus of claim 16 wherein the valve member has a first and a second position, the means for selectively placing comprising a fifth channel and a sixth channel, the fifth channel providing fluid communication between the first channel, the second channel, and the third channel when the valve member is in the fist position and the sixth channel providing fluid communication between the third channel and the fourth channel when the valve member is in the second position.

18. The apparatus of claim 17 further comprising a one-way valve in fluid communication with the outer port of the first channel, the one-way valve permitting fluid to pass through the outer port and into the first channel.

19. The apparatus of claim 16 further comprising means for storing blood that is withdrawn from the body.

20. The apparatus of claim 16 wherein the means for storing blood is a bag that is in fluid communication with the outer port of the second channel, the bag being detachable.

* * * * *